United States Patent
Glass et al.

(10) Patent No.: US 10,430,722 B2
(45) Date of Patent: Oct. 1, 2019

(54) LEARNING PARAMETERS IN A FEED FORWARD PROBABILISTIC GRAPHICAL MODEL

(71) Applicant: International Business Machines Corporation, Armonk, NY (US)

(72) Inventors: Michael R. Glass, Bayonne, NJ (US); James W. Murdock, IV, Amawalk, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 723 days.

(21) Appl. No.: 14/948,697

(22) Filed: Nov. 23, 2015

(65) Prior Publication Data

US 2017/0061301 A1    Mar. 2, 2017

Related U.S. Application Data

(63) Continuation of application No. 14/842,022, filed on Sep. 1, 2015.

(51) Int. Cl.
*G06N 20/00* (2019.01)
*G06N 7/00* (2006.01)
(Continued)

(52) U.S. Cl.
CPC ............ *G06N 20/00* (2019.01); *G06F 19/30* (2013.01); *G06N 5/04* (2013.01); *G06N 5/046* (2013.01); *G06N 7/005* (2013.01)

(58) Field of Classification Search
CPC .................................................... G06N 5/045
See application file for complete search history.

(56) References Cited

U.S. PATENT DOCUMENTS

| | | | | |
|---|---|---|---|---|
| 5,265,065 A | * | 11/1993 | Turtle | G06F 17/30011 |
| 2011/0119212 A1 | * | 5/2011 | De Bruin | A61B 5/00 706/12 |
| 2013/0029307 A1 | * | 1/2013 | Ni | G06N 99/005 434/322 |

OTHER PUBLICATIONS

Berant, Jonathan, et al., Semantic Parsing on Freebase from Question-Answer Pairs (Oct. 2013), Proc. of the 2013 Conference on Empirical Methods in Natural Language Processing, pp. 1533-1544 (Year: 2013).*

(Continued)

*Primary Examiner* — Alan Chen
(74) *Attorney, Agent, or Firm* — Cantor Colburn LLP; Kevin Michael Jordan

(57) ABSTRACT

According to an aspect, learning parameters in a feed forward probabilistic graphical model includes creating an inference model via a computer processor. The creation of the inference model includes receiving a training set that includes multiple scenarios, each scenario comprised of one or more natural language statements, and each scenario corresponding to a plurality of candidate answers. The creation also includes constructing evidence graphs for each of the multiple scenarios based on the training set, and calculating weights for common features across the evidence graphs that will maximize a probability of the inference model locating correct answers from corresponding candidate answers across all of the multiple scenarios. In response to an inquiry from a user that includes a scenario, the inference model constructs an evidence graph and recursively constructs formulas to express a confidence of each node in the evidence graph in terms of its parents in the evidence graph.

6 Claims, 6 Drawing Sheets

(51) Int. Cl.
   *G06N 5/04*     (2006.01)
   *G06F 19/00*    (2018.01)

(56) References Cited

OTHER PUBLICATIONS

Lally, Adam, et al., WatsonPaths: Scenario-based Question Answering and Inference over Unstructured Information (Sep. 17, 2014 ), IBM Research Report, pp. 1-20 (Year: 2014).*
Tanenbaum, Andrew, Structured Computer Organization, 2nd Ed. (1984), N.J., Prentice-Hall, pp. 10-12 (Year: 1984).*
List of IBM Patents or Patent Applictions Treated as Related; (Appendix P), Filed Jan. 28, 2016, 2 pages.
Michael R. Glass, et al., Pending U.S. Appl. No. 14/842,022 entitled "Learning Parameters in a Feed Forward Probabilistic Graphical Model," filed with the U.S. Patent and Tradmark Office on Sep. 1, 2015.

* cited by examiner

LEARNING PARAMETERS IN A FEED FORWARD PROBABILISTIC GRAPHICAL MODEL

DOMESTIC PRIORITY

This application is a continuation of U.S. patent application Ser. No. 14/842,022, filed Sep. 1, 2015, the content of which is incorporated by reference herein in its entirety

BACKGROUND

The present disclosure relates generally to question answering computer systems, and more specifically, to learning parameters in a feed forward probabilistic graphical model.

Question answering (QA) is a type of information retrieval. Given a collection of documents, a system employing QA attempts to retrieve answers to questions posed in natural language. QA is regarded as requiring more complex natural language processing (NLP) techniques than other types of information retrieval, such as document retrieval. An inquiry to a QA system can be in the form a question that includes a single sentence or phrase in natural language (e.g., English) or a formal language (e.g., first order logic) that intends to ask for the end point(s) of a relation or to ask whether or not a relation between two concepts is true. An inquiry can also be in the form of a natural language statement or scenario, which may represent several factors that should be taken into account when searching for an answer. A QA system can model the question and possible answers as an inference model that includes an inference graph.

An inference graph is a feed forward probabilistic graphical model that is useful for formalizing relationships about uncertain events in the world. For example, an inference model with nodes "patient has fever", "patient has flu", and "patient is fatigued" can be built. Edges in the graph reflect the way that these events are related; for example, knowing that that a patient has the flu should cause someone to suspect that the patient probably has a fever. In an inference graph the probability of any node is conditionally independent of the probability for all other nodes, given the probability of its parents.

SUMMARY

Embodiments include a method, system, and computer program product for learning parameters in a feed forward probabilistic graphical model. A method includes creating an inference model via a computer processor. The creating includes receiving a training set that includes multiple scenarios, each scenario comprised of one or more natural language statements, and each scenario corresponding to a plurality of candidate answers. The creating also includes constructing evidence graphs for each of the multiple scenarios based on the training set, and calculating weights for common features across the evidence graphs that will maximize a probability of the inference model locating correct answers from corresponding candidate answers across all of the multiple scenarios. In response to an inquiry from a user via the computer processor, where the inquiry includes a scenario, the inference model constructs an evidence graph and recursively constructs formulas to express a confidence of each node in the evidence graph in terms of its parents in the evidence graph.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
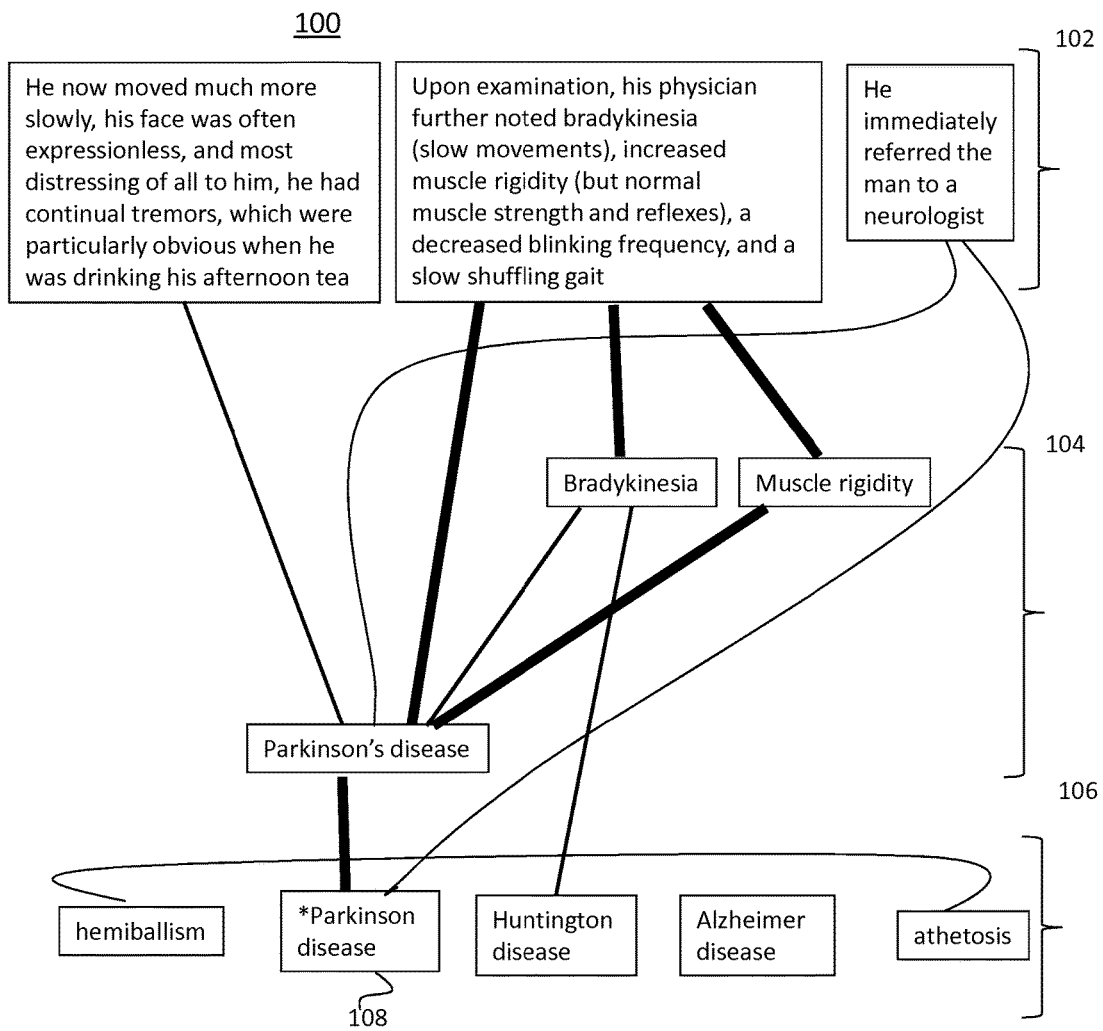
FIG. 1 depicts an evidence graph in accordance with an embodiment.

Embodiments described herein include a method for learning parameters in an inference graph in which ground truth is not available on intermediate nodes. This is often true in real-world applications where nodes with no parents (root nodes) often correspond to observable facts about a case, and nodes with no descendants (terminal nodes) often correspond to conclusions in that case. It is relatively easy to find cases where there is human ground truth (i.e., things that are known) for observations and conclusions. For example, sample exams for medical licensing often include a question with observable facts (root nodes) and an answer key with correct final conclusions (terminal nodes) but no information about intermediate conclusions (intermediate nodes) that an inference process would use to arrive at the final conclusion. Edges between nodes can represent relations and have associated probabilities that are functions of parameters. The parameters can be learned based on the other nodes in the inference graph. Embodiments described herein provide a method for recursively constructing formulas for expressing the confidence in each node in terms of the information from its parent nodes.

As used herein, the term "parameter" refers to a real valued number controlling the inference of a model, such as the weight for a feature.

Embodiments assign values for parameters so that the resulting model for edge confidence minimizes the loss function on the terminal nodes. These parameters can be features from a QA system, expressing different sources of confidence for the existence of the edge. In a QA application of embodiments, the terminal nodes are the candidate answers. In embodiments, a combining function, "c", is employed to take a set of input confidences and produce an output confidence; P(n) is the set of parent nodes; and m_theta(<x;y>) is the edge confidence in the edge from x to y provided by the model with parameters theta. For all nodes "n" such that P(n) is the empty set (i.e., parent nodes), the confidence in that node, p_theta(n), is provided as input. In some instantiations, p_theta(n) will be 1 for all such cases (i.e., nodes without parents are direct observations that are known to be true with complete certainty). Then the confidence in nodes that have parents (i.e., for which P(n) is not the empty set) can be defined as:

p_theta(n)=c({p_theta(a)*m_theta(<a;n>)|a in P(n)}).

Embodiments recursively construct a formula expressing the confidence in each node in terms of its parent nodes in the inference graph. In this embodiment, the confidence contributed by an edge is the edge confidence multiplied by the confidence in the "from" node, where the edge confidence is a function of the parameters. The root nodes, those without parents, are taken as evidence and have a known confidence (e.g., taken as evidence with a confidence of 1), which is provided as input.

In the case of an inference graph based on noisy-OR, the combining function for confidence in a node can be calculated as the noisy-OR of all edge confidences. A node may be the ancestor of many other nodes, and in this case the formula for that node can be represented only once so that all descendants of the node share the same formula for its confidence. The formulas for confidence in the terminal nodes and the ground truth for the terminal nodes can then be used as input to a loss function, such as a negative log-likelihood The parameters for edge weights can then be learned by optimization techniques such as, but not limited to: non-convex optimization techniques; direct optimization techniques; and gradient based optimization techniques.

An embodiment that is applied to training a model for clinical diagnosis in the medical field is described herein. It should be noted that embodiments are not limited to clinical diagnosis or to the medical field as they may be applied to any applications where an inquiry is in the form of a statement or scenario description such as, but not limited car repair diagnosis, and computer help desk support. Embodiments can be applied to any application that uses an inference graph, where a ground truth is not available on intermediate nodes.

Answering a diagnosis question about a complex clinical scenario requires combining the evidence from many simpler sub-questions. Embodiments disclosed herein provide models of inference and learning that can produce accurate and calibrated confidences for candidate diagnoses using an inference graph constructed from the sub-question evidence. Compared to a baseline system using a different set of factoid questions as training data for sub-question confidence, improved performance can be realized by learning weights for sub-question features based only on final answer ground truth for the diagnosis question.

Traditional QA systems typically focus on short-answer questions, sometimes called factoid questions, such as "skeletal finding on chest x-ray in patient with aortic coarctation." The question is a single sentence and the answer is a single term or entity. In contrast, diagnostic questions present a scenario (e.g., a clinical picture describing a patient) and then ask for the most likely diagnosis.

The term "inference graph" as used herein refers to any graph represented by a set of nodes connected by edges, where the nodes represent statements and the edges represent relations between statements. An inference graph can be used to represent relation paths between factors in an inquiry and possible answer to that inquiry. An inference graph is multi-step if it contains more than one edge in a path from a set of factors to an answer. In an embodiment, graph nodes, edges/attributes (confidences), statements and relations may be represented in software, as Java objects. Confidences, strengths, and probabilities are attached to them for processing by various computer systems.

As described herein, embodiments include answering scenario questions by constructing a graph that links factors extracted from the scenario (e.g., symptoms or lab values) to candidate diagnoses. Edges can be added to this graph by using a factoid QA subsystem to answer questions about existing nodes. For example, the system may ask what diseases cause particular symptoms. Each edge has a confidence value and a vector of features assigned by the underlying factoid QA system. As used herein, the term "feature" refers to a number summarizing a relevant aspect of the task. As used herein, the term "vector of features" refers to any collection of features. Embodiments estimate the confidence in each candidate diagnosis, which depends on the strength and structure of its connection to the factors.

Embodiments described herein provide alternative models of inference where the confidence in each candidate diagnosis is expressed as a quickly evaluable, parameterized mathematic expression matching the semantics of the inference graph. Parameters, and combinations of parameters, are learned for these models using only ground truth on the final diagnosis answers. In embodiments, structures of inference graphs are fixed per instance (e.g., a graph representing one scenario and answer), but can vary dramatically across training instances (e.g., a plurality of graphs representing two or more scenarios and associated answers). Embodiments learn one set of parameters that performs well across all the training instances of the inference graphs. The edge strengths are expressed as functions of the parameters shared across the edges.

In an example described herein, training and evaluation are performed on a medical test preparation question set that can include multiple choice medical diagnosis problems from an unstructured or semi-structured, natural language description of a patient. An example diagnosis question is provided below.

A 73-year-old retired nurse had finally convinced her husband, a 75-year-old retired English teacher, to see a physician for his condition. Over the past several years, the man had experienced a gradual decline in his ability to initiate and perform simple voluntary movements. He now moved much more slowly, his face was often expressionless, and most distressing of all to him, he had continual tremors, which were particularly obvious when he was drinking his afternoon tea. Upon examination, his physician further noted bradykinesia (slow movements), increased muscle rigidity (but normal muscle strength and reflexes), a decreased blinking frequency, and a slow shuffling gait. He immediately referred the man to a neurologist. Which of the following disorders is the MOST likely diagnosis? A) hemiballism; B) Parkinson disease; C) Huntington disease; D) Alzheimer disease; E) athetosis.

Turning now to FIG. 1, a simplified evidence graph 100 is generally shown in accordance with an embodiment. The simplified evidence graph 100 is built based on an inquiry that includes a diagnostic question scenario 102 and a plurality of candidate answers 106. As shown in FIG. 1, factors 104 are extracted from the scenario 102 using, for example, one or more parsers, entity recognizers, relation detectors, and co-reference resolvers. With respect to the candidate answers 106, only one answer 108 is identified as being correct based on the scenario 102. The candidate answers 106 can be represented as terminal nodes in an inference graph.

As used herein, a "factor" is a logically independent element of an inquiry and can be represented as a root node in an inference graph. Examples of factors 104 shown in FIG. 1 include "bradykinesia (slow movements)" and "muscle rigidity." In addition, factors can be weighted, as some factors may be more important than others in finding and scoring an answer. Various techniques are possible for initializing the confidence weighting in each factor. For example, the factor with the most unique terms relative to the domain may be given a higher weight than other factors. Known techniques including inverse document frequency (IDF) can be used for producing weights for each of the factors.

Natural language sub-questions can be generated from each of the factors. For example, a question "What causes X" where X is one of the factors can be formed. Other relations can also be used to generate sub-questions such as, but not limited to: "indicates", "is associated with", and "treats." Other embodiments might produce more straightforward and grammatical questions, for example by applying question generation patterns or templates. These questions are submitted to the QA system, producing answers with features generated by the QA system in FIG. 5. These answers are incorporated as intermediate nodes in the inference graph.

Two systems of inference without learning may be utilized in facilitating the embodiments described herein. The first transforms the evidence graph into a feed forward noisy-or network. The second approaches the problem of confidence estimation as probabilistic inference over a graphical model.

The noisy-or model is based on the intuition that symptoms and findings indicate diseases, and therefore a diagnosis is indicated if any of the clinical factors indicate it. Using a noisy-or to combine probabilistic causation or indication may be a desired approach when training data is scarce or unavailable. In the evidence graph described above, the data is unavailable, since ground truth is not provided for the intermediate nodes.

Throughout this description, the logical-or notation v, V is used to indicate probabilistic, noisy-or.

$$\bigvee_{s \in S} s = 1 - \prod_{s \in S} 1 - s$$

Figure 2:
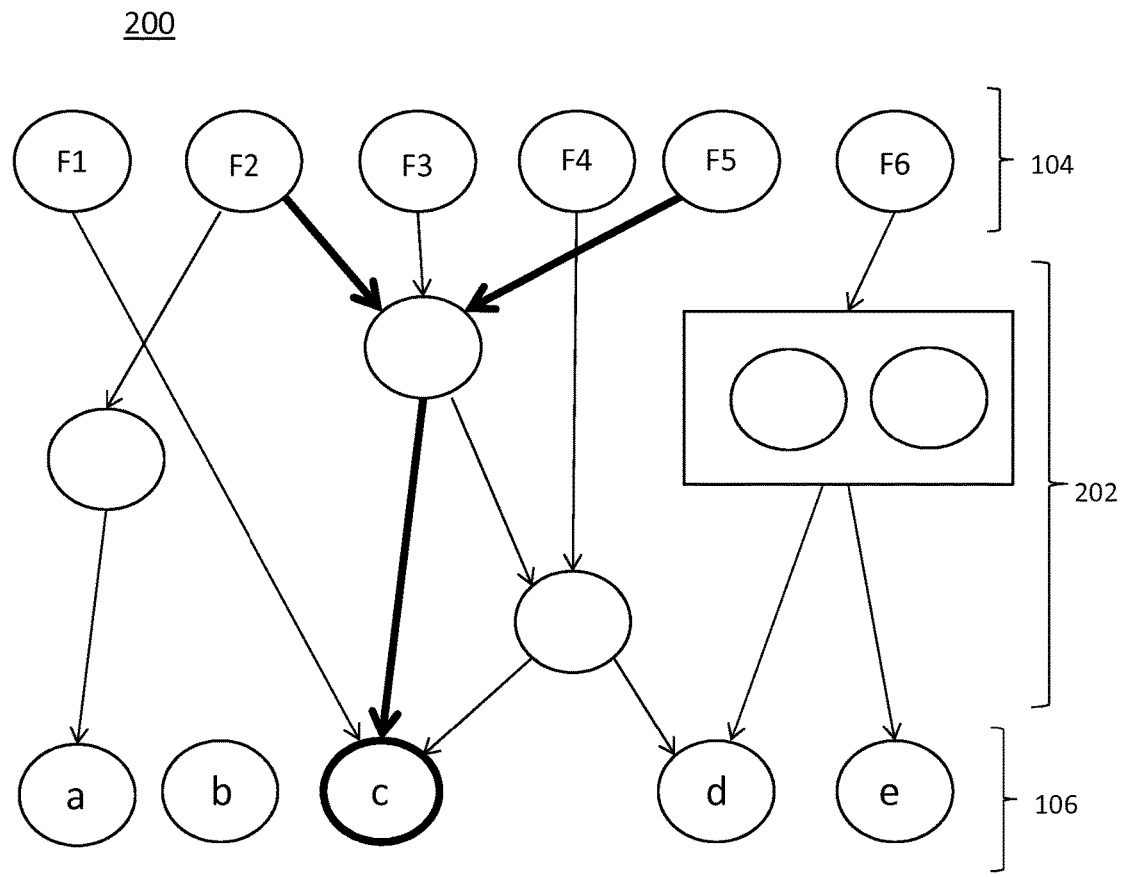
FIG. 2 depicts a directed acyclic graph (DAG) in accordance with an embodiment.

As shown in FIG. 2, a directed acyclic graph (DAG) 200 is generated from an evidence graph, whereby the evidence graph is transformed into a feed-forward model in which matching nodes are clustered and cycles are broken by re-orienting edges to point from factors to candidates, producing a directed acyclic graph (DAG). A layer 202, shown between the factors 104 and candidate answers 106, illustrates this aspect. The confidence in clinical factors (factors 104) is 1.0. For all other nodes the confidence is defined recursively in terms of the confidences of the parents and the confidence of the edges produced by the system. Let the set of parents for a node n be given by a(n). The confidence the QA system gives for one node, m, indicating another, n, is given by c(m,n). Then the confidence for non-clinical factor nodes is given below.

$$P(n) = \bigvee_{a_i \in a(n)} c(a_i, n) \cdot P(a_i)$$

Another method avoids the need to transform the evidence graph into a DAG. The belief engine casts the problem of probabilistic inference as marginal inference in a factor graph. Each node is a Boolean random variable and the factors in its Markov blanket are constructed from the sub-question confidences.

In an embodiment, systems of inference may be utilized that include a noisy-OR model with learning. A logistic model is developed for features of the QA system. In the embodiments described herein, σ(x) is used to indicate the sigmoid function.

$$\sigma(x) = \frac{1}{1 + e^{-x}}$$

The feature vector the QA system gives for one node, m, indicating another, n, is given by λ(m,n). The learned weight vector for the QA features is $\vec{q}$.

$$P(n) = \bigvee_{a_i \in a(n)} \sigma(\vec{q} \cdot \lambda(a_i, n)) \cdot P(a_i)$$

The noisy-OR combination can be utilized when the sources of evidence are independent. When there are two edges leading from the same inference node (which may be the result of merging two or more evidence graph nodes) to the node under consideration, these edges are combined by taking the maximum of the inputs, rather than combining by noisy-OR. The edge type variation of the noisy-OR model considers the type of the edge when propagating confidence from parents to children. The strength of the edge according to the QA model is multiplied by a per-edge-type learned weight, then, a sigmoid function is applied. The type of the edge is determined by the type of sub-question asked. For example, edge types could be symptom, indicates, or treats. In this way, different types of sub-questions may have different influences on confidences, even when the QA model produces similar features for them. The type of the edge from m to n is given by (m, n) and its learned weight is $\omega_{\gamma(m,n)}$.

$$P(n) = \bigvee_{a_i \in a(n)} \sigma(w_{\gamma(a_i, n)} \cdot c(a_i, n)) \cdot P(a_i)$$

Another model that can be implemented by embodiments is a feature addition model, which explores another combination function in the recursive definition of confidence. As in the noisy-OR model, confidence in the clinical factors is 1.0, but confidence in the intermediate nodes is given by adding the feature values for the questions that lead to it then applying the logistic model to the resulting vector.

The effect is that the confidence for a node does not increase monotonically with the number of parents. Instead, if features that are negatively associated with correctness are present in one sub-question edge, it can lower the confidence of the node below the confidence given by another sub-question.

$$P(n) = \sigma\left(\vec{q} \cdot \sum_{a_i \in a(n)} \lambda(a_i, n) \cdot P(a_i)\right)$$

In embodiment of a matching model, forward questions are asked from the clinical factors and also backward questions are asked from the candidate diagnoses. In the matching model, the intuition that the answers from the forward questions should match either the correct diagnosis or the answers to the backward questions about it is formalized. Similarly, the answers to the backward questions about the correct diagnosis should match either the clinical factors or the answers to the forward questions.

The clinical factors plus the answers to the forward questions about them form a set of terms F'. Each of these terms has a weight summarizing its importance or relevance for the scenario w(f'). For each candidate diagnosis there is another set of terms, the diagnosis itself and the answers to the backwards question about it D'(d). These terms each have a weight indicating its importance or relevance for the diagnosis w(d').

Using a set of term matchers such as WordNet and the Unified Medical Language System (UMLS) based term matchers, the degree to which two terms match is estimated as match(f', d').

$$P(d) = \frac{\sum_{f' \in F'} \left( w(f') \cdot \max_{d' \in D'(d)} w(d') \cdot match(f', d') \right)}{\sum_{f' \in F'} w(f')}$$

Weights are based on a single logistic model, in the case of terms provided directly by the question, or the product of two logistic models in the case of answers to sub-questions. In each case, one logistic model is based on the type of the term, given as a one-hot vector μ(n). The other model is based on QA features. The vectors $\vec{q}$ and $\vec{\omega}$ are learned.

$$w(n) = \begin{cases} \sigma(\vec{w} \cdot \mu(n)) & \text{if } n \in F \cup D \\ \sigma(\vec{w} \cdot \mu(n)) \cdot \sigma(\vec{q} \cdot \lambda(a, n)) & \text{otherwise} \end{cases}$$

The match is also a logistic model, based on a collection of term matches.

Figure 3:
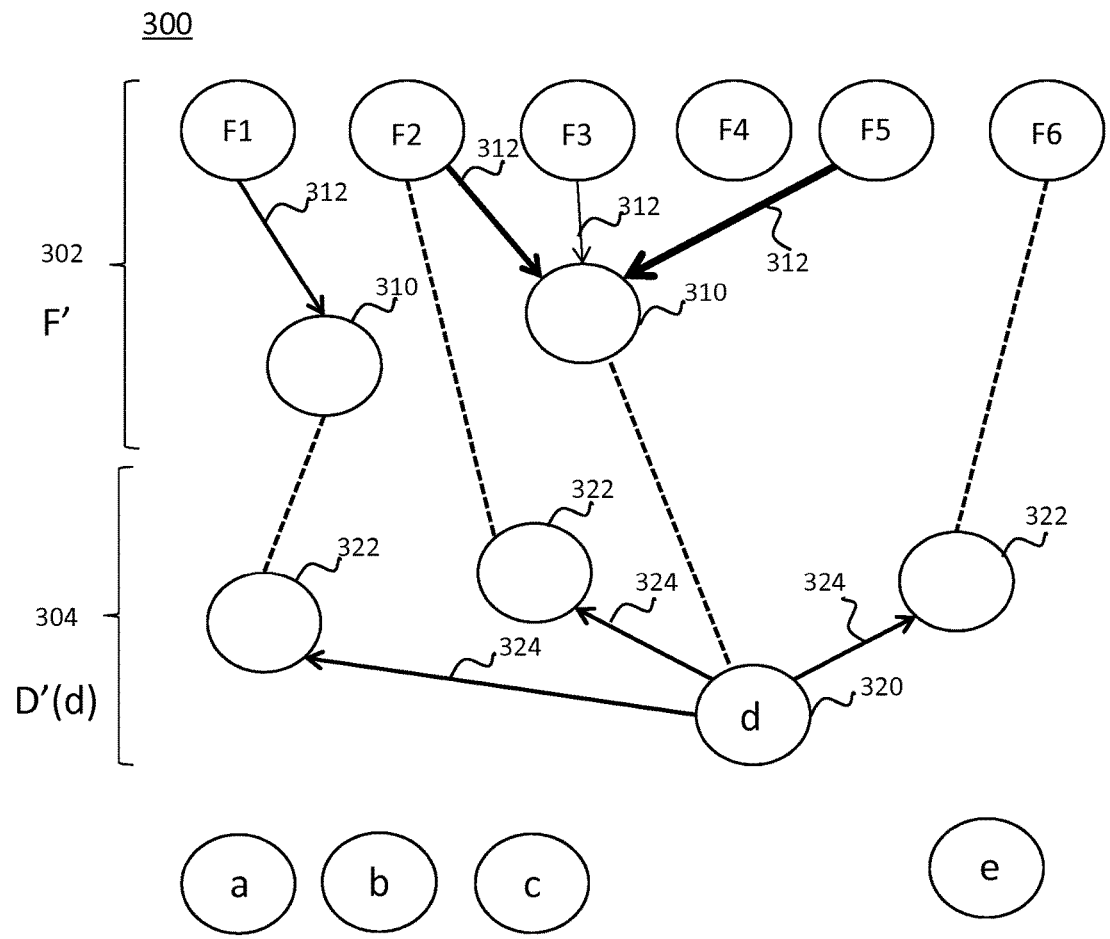
FIG. 3 depicts a matching model view of an evidence graph in accordance with an embodiment.

Turning now to FIG. 3, a matching model view 300 of an evidence graph is generally shown in accordance with an embodiment. In an embodiment, the evidence graph may be a directed acyclic graph. As shown in FIG. 3, clinical factors F1-F6 and answers 310 to the forward questions about them form a set of terms 302. Each of these terms 302 has a weight 312 summarizing its importance or relevance for the scenario. Also, as shown in FIG. 3, another set of terms 304 is depicted. This set of terms includes diagnosis 320 and the answers 322 to the backwards questions about it. Each of these terms 304 likewise has a weight 324 indicating its importance or relevance to the diagnosis. The weights may be expressed in the model as lines of varying thickness, in which the thicker the line, the heavier the weight is given.

An embodiment also supports a causal model, which is based on the intuition that a correct diagnosis should explain all of the patient's symptoms and findings. For some clinical factors, such as demographic information, the diagnosis should simply be consistent with the factor. Two probabilities to estimate can include the probability that a diagnosis explains a clinical factor $\sigma(\vec{q} \cdot \lambda(d, f))$ and a probability that a clinical factor is an unexplained or irrelevant observation, i.e., a leak. Features from the QA system may be used to estimate the degree that a candidate explains a factor and features of the clinical factor to estimate the lead probability $\sigma(\vec{\omega} \cdot \mu(f))$.

The raw confidence in each candidate is given by the equation below:

$$P(d) = \prod_{f \in F} \sigma(\vec{q} \cdot \lambda(d, f)) \vee \sigma(\vec{w} \cdot \mu(f))$$

The confidence for each candidate is given by the product over every clinical factor of the probability that either the diagnosis explains the factor, or the factor leaked (an unexplained observation or irrelevant).

Another model that can be implemented by embodiments is a confidence re-estimation model. In the previously described inference systems, there is no constraint that the answer confidences sum to one. In the confidence re-estimation model, a process is performed where features based on the raw confidence from the inference model are transformed into a proper probability distribution over the candidate answers. The features that can be used in this confidence re-estimation are: the raw answer confidence, the log it of the raw answer confidence, the normalized answer confidence and its log it, and the rank of the answer. Additionally, if it is the most confident answer, the gap between its confidence and the second most confident answer is a feature, otherwise the gap between it and the most confident answer is used as a feature.

For each answer, its confidence is proportional to the exponentiated dot product of the feature vector based on the model confidence for the diagnosis $\vec{m}_d$, and a learned weight vector $\vec{c}$, a maxent model.

$$P(d') = \frac{1}{Z} \exp(\vec{m}_{d'} \cdot \vec{c})$$

$$Z = \sum_{d \in D} \exp(\vec{m}_d \cdot \vec{c})$$

Turning now to learning in diagnosis graphs, the above-referenced models for inference all depend on the strengths of edges created from the answers to sub-questions. Estimating these strengths can be difficult because there is no ground truth for the answers to these sub-questions, only for the final answer.

One of the techniques used by embodiments is to train a sub-question model based on Doctor's Dilemma™ (DD) questions, which have been developed by the American College of Physicians (SM). Doctor's Dilemma provides a set of factoid questions used to assess medical knowledge. The model was trained from a set of 1039 DD questions and its associated answer key. This is referred to herein as the DD model.

While the DD questions do have some basic similar to the sub-questions asked in evidence graphs, there are important differences. In an evidence graph sub-question, there is always one known entity and one relation that is being asked about. For DD, the question may constrain the answer by multiple entities and relations. A sub-question, like "What does hypertension indicate" has many correct answers, while DD questions have a single best answer. Additionally, there may be a mismatch between how confidence for DD is trained and how sub-question confidence is used in an inference method. The DD confidence model is trained to maximize log-likelihood on a correct/incorrect binary classification task. In contrast, many probabilistic models use confidence as something like strength of indication or relevance.

Additionally, some inference models have parameters that are not based on sub-questions. For example, the matching model develops a model for the degree two nodes match and the importance of a given node. A simple baseline for node importance is to give all nodes either equal weight or a weight based on a single simple statistic, such as IDS (inverse document frequency). A simple model for matching can take the confidence from a single term matcher, thought to be generally effective.

Figure 4:
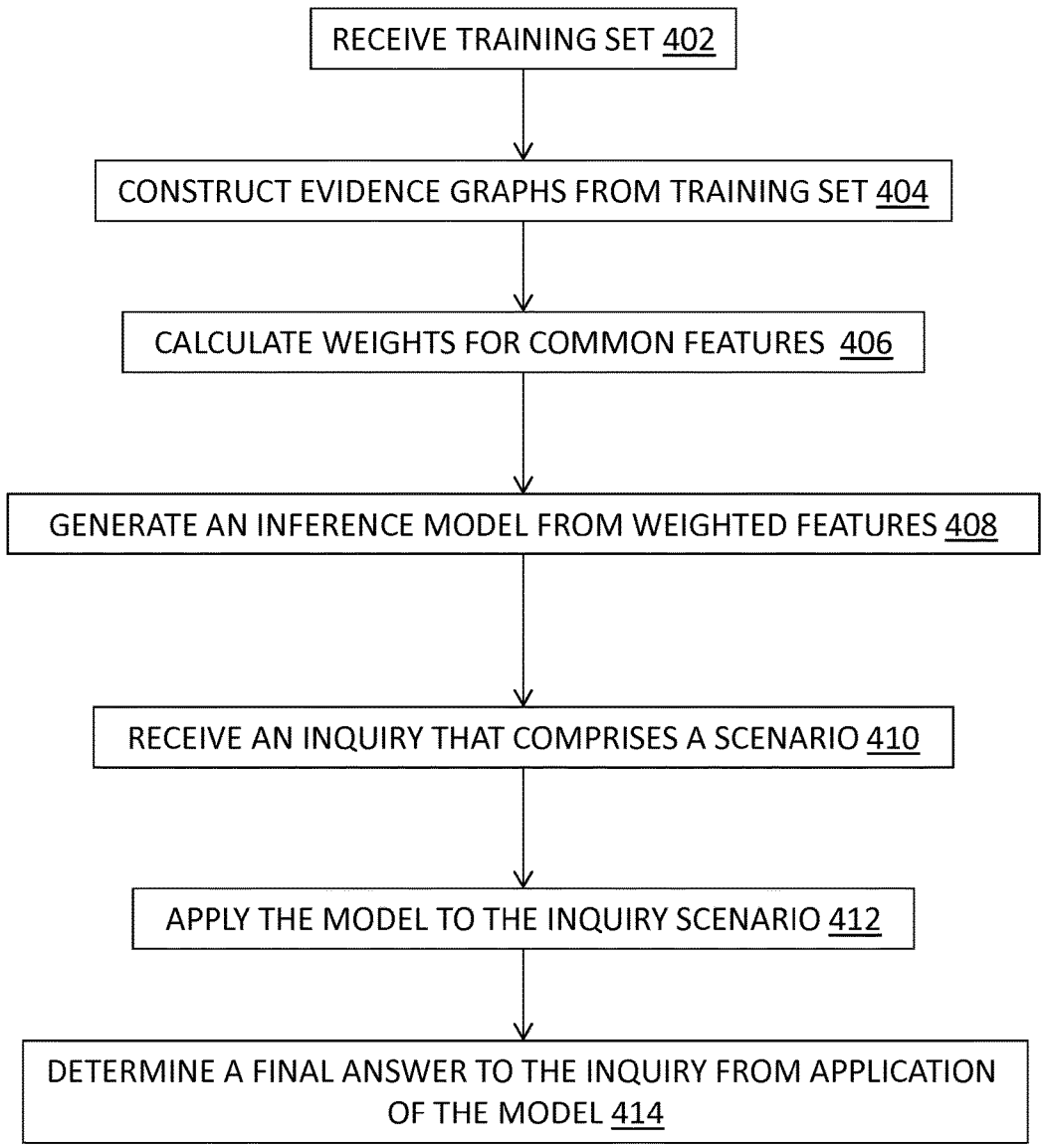
FIG. 4 depicts a process flow for learning parameters in a feed forward probabilistic graphical model in accordance with an embodiment.

To address the limitations of the DD model, methods for learning a new model for sub-question features as well as weights for non-sub-question features are implemented by embodiments. One goal is to produce a probability distribution over the multiple choice answers with as much of the mass as possible concentrated on the correct answer. Turning now to FIG. 4, a process flow 400 for learning parameters in a feed forward probabilistic graphical model is generally shown in accordance with an embodiment. At block 402, a training set is received, and at block 404 evidence graphs are constructed (e.g., via a QA system) in one or more of the manners described previously. In embodiments, the evidence graphs that are constructed contain different nodes and edges, even different numbers of nodes and edges. These graphs do share features, such as QA features (e.g., topic similarity, string kernel, search rank), matching features (e.g., substring matching, Wikipedia redirects), and node type features (e.g., Disease, Anatomy).

At block, 406, weights are calculated for the common features (e.g., QA features, matching features, node type features) shared across all evidence graphs that maximize performance over the training set. For each inference model, it is possible to transform an evidence graph e into a function mapping the values of the weights to confidence in the correct diagnosis $\Phi_e : \mathbb{R}^n \to \mathbb{R}$. By construction, all inference models described previously have fast, exact inference. The models permit expressing the confidence in the correct answers as a closed form expression. Summing the log of the confidence in the correct diagnosis across the training set T, results in constructing a learning problem with log-likelihood in the correct final answers as the objective function. The result is a function that is nonconvex, and in some cases (due to max) not differentiable in the parameters.

To limit overfitting and encourage a sparse, interpretable parameter weighting, L1-regularization is used. The absolute value of all learned weights is subtracted from the objective function.

$$\vec{u}^* = \underset{\vec{w} \in \mathbb{R}^n}{\mathrm{argmax}} - \|\vec{w}\|_1 + \sum_{i \in T} \log(\Phi_t(\vec{w}))$$

To learn the parameters for the inference models, a 'black-box' optimization method, such as greedy-stochastic local search can be applied. This is a method of direct search that considers a current point in $p \in \mathbb{R}^n$ and a neighborhood function mapping points to subsets of $\mathbb{R}^n \mathcal{N} : \mathbb{R}^n \to \mathbb{R}$ ( $\mathcal{P}^n$). Additionally, the optimization procedure maintains p*, the best known point. From the current point, a new point p' is randomly selected from $\mathcal{N}(p)$. If the change improves the objective function it is kept; if the change worsens the object function it is accepted with some probability ϵ. In this way, the learning explores the parameter space, tending to search in regions of high value while never becoming stuck in a local maximum.

Embodiment utilized a neighborhood function $\mathcal{N}$ related to compass search. A single parameter or a pair of parameters is selected to change by some δ. Additionally, due to the L1 regularization, the neighborhood permits setting any single parameters to zero, encouraging sparse solutions.

There is no straight-forward stopping criteria for this search, and in an embodiment it is limited by time.

Not every $\Phi_t$ depends on every element of $\vec{\omega}$. Even in cases where $\Phi_t$ depends on $\vec{\omega}$, many pieces of the function may not. To enable efficient re-computation, a preprocessor can construct for weight $\vec{\omega}$ a DAG indicating which parts of functions will need to be recomputed, and in what order, if that weight is changed. Unchanged function parts return their cached value if used in the computation of a part that does change.

Each of the multiple inference models, approaches the problem of combining the sub-question confidences from a different intuition and formalizes it in a different way. To combine these different approaches an ensemble can be trained. This is a final, convex, confidence estimation over the multiple choice answers using the predictions of the inference models as features.

The ensemble learning uses the same training set that the individual inference models use. To avoid giving excess weight to inference models that have over fit the training set, a common technique from stacking ensembles can be utilized. The training set is split into five folds, each leaving out 20% of the training data—as though for cross validation. Each inference model is trained on each fold. When the ensemble gathers an inference model's confidence as a feature for an instance, the inference model uses the learned parameters from the fold that excludes that instance. In this way, each inference models performance is test-like and the ensemble model does not overly trust overfit models.

The ensemble can be a binary logistic regression per diagnosis candidate using three features from each inference model that was developed. In an embodiment, the features used include: the probability of the candidate diagnosis, the log it of the probability, and the rank of the diagnosis among the multiple choice answers. Using the log of the probability ensures that selecting a single inference model is in the ensemble's hypothesis space, achieved by simply setting the weight for that model's log it feature to one and all other weights to zero.

Each inference model is also trained on the full training set, these versions are applied at test time to generate the features for the ensemble. Referring back to FIG. 4, at block 408, an inference model is generated from the results of steps 402-406. The inference model is ready for use by a question answering system.

At block 410, an inquiry is received which includes a scenario. For example, in the medical field embodiment described above, the inquiry may be a group of statements, observations, symptoms, etc. of a patient. At block 412, the inference model is applied to the scenario submitted as the inquiry, and at block 414, a final answer is determined from application of the inference model based on the common features and weights assigned thereto. In the medical field embodiment, for example, the final answer may be a diagnosis for the patient that is believed to be most probable (i.e., most accurate).

Figure 5:
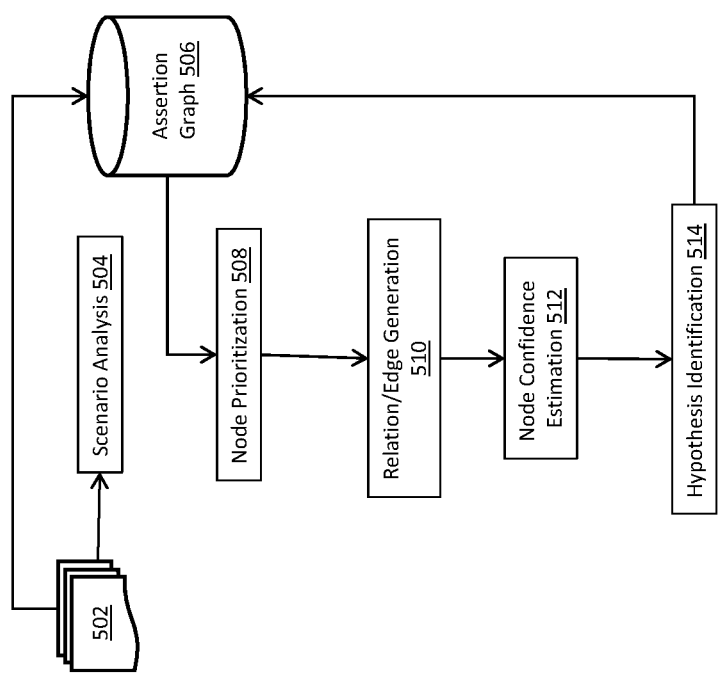
FIG. 5 depicts a high-level block diagram of a framework where embodiments of learning parameters in a feed forward probabilistic graphical model can be implemented in accordance with an embodiment.

FIG. 5 depicts a framework in which one embodiment of learning parameters in a feed forward probabilistic graphical model may be implemented. The framework of FIG. 5 is implemented by the WatsonPaths™ product from IBM. WatsonPaths is a cognitive computing tool that enables natural language interaction between medical professionals, data, and electronic medical records. The WatsonPaths tool enables users to easily understand both structured and unstructured data from various data sources and also understand the pathway taken by the tool in identifying solutions or answers to questions asked by the users.

Information 502 from a data source may include a scenario, such as a medical case or observations noted regarding a patient. An analysis of the scenario is conducted 504. For example, the scenario may be broken down into statements or pieces that can be individually analyzed. An assertion graph 506 is generated from the results of the analysis. The nodes in the graph are directed to features derived from the analysis. The nodes are prioritized 508 according to their relevance, as determined from the analysis. Likewise, edges of the graph are generated 510 from the analysis and are directed to relationships among the nodes.

Confidences in the nodes are estimated 512 and a hypothesis is identified 514 from the confidences. The exemplary embodiments, as described above, learn parameter values in support of the estimation of the confidences in the nodes 512. The hypothesis 514 may then be fed back to the assertion graph 506, which then re-prioritizes the nodes 508 based on updates to the assertion graph 506. The process cycle from block 514, block 506, and block 508 may be repeated until, e.g., a desired outcome or solution is reached.

Figure 6:
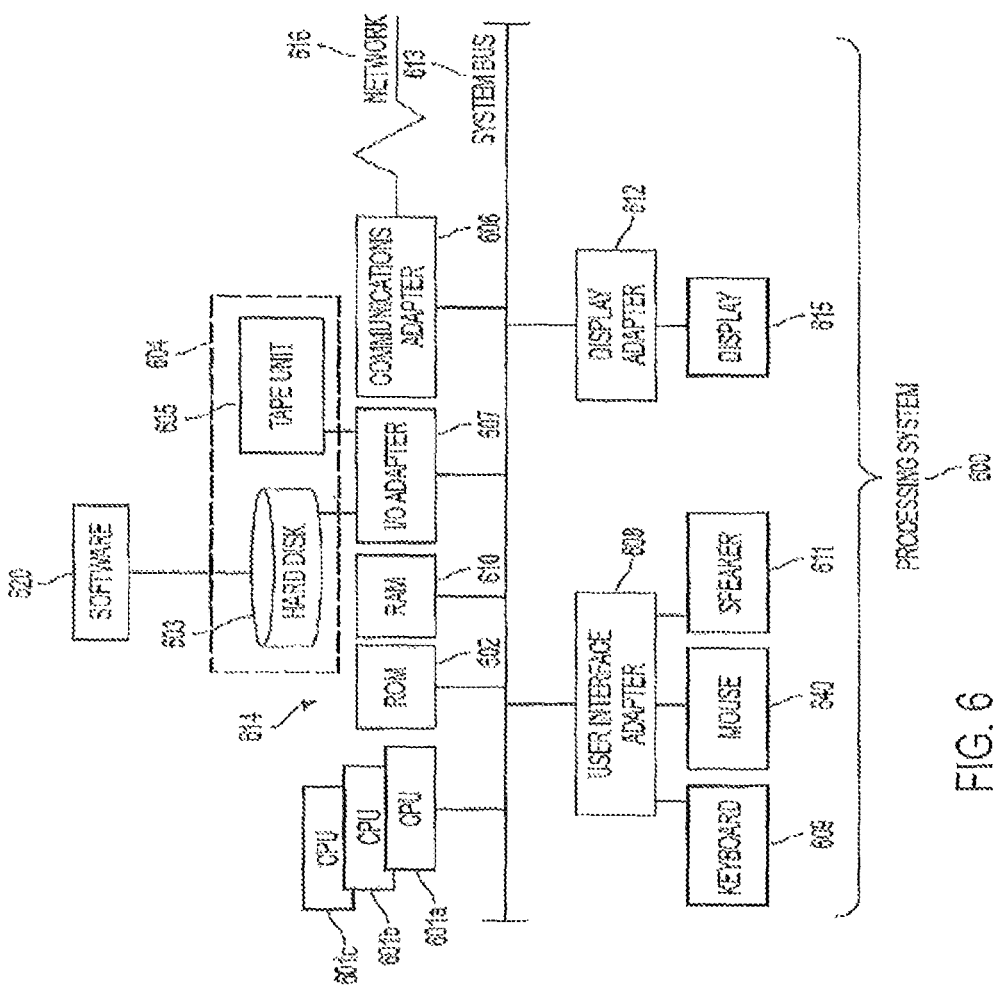
FIG. 6 depicts a processing system for learning parameters in a feed forward probabilistic graphical model in accordance with an embodiment.

FIG. 6 depicts a processing system for learning parameters in a feed forward probabilistic graphical model in accordance with an embodiment.

Referring now to FIG. 6, there is shown an embodiment of a processing system 600 for implementing the teachings herein. In this embodiment, the processing system 600 has one or more central processing units (processors) 601a, 601b, 601c, etc. (collectively or generically referred to as processor(s) 601). Processors 601 are coupled to system memory 614 and various other components via a system bus 613. Read only memory (ROM) 602 is coupled to system bus 613 and may include a basic input/output system (BIOS), which controls certain basic functions of the processing system 600. The system memory 614 can include ROM 602 and random access memory (RAM) 610, which is a read-write memory coupled to system bus 613 for use by processors 601.

FIG. 6 further depicts an input/output (I/O) adapter 607 and a network adapter 606 coupled to the system bus 613. I/O adapter 607 may be a small computer system interface (SCSI) adapter that communicates with a hard disk 603 and/or tape storage drive 605 or any other similar component. I/O adapter 607, hard disk 603, and tape storage drive 605 are collectively referred to herein as mass storage 604. Software 620 for execution on processing system 600 may be stored in mass storage 604. Network adapter 606 interconnects system bus 613 with an outside network 616 enabling processing system 600 to communicate with other such systems. A screen (e.g., a display monitor) 615 is connected to system bus 613 by display adapter 612, which may include a graphics controller to improve the performance of graphics intensive applications and a video controller. In one embodiment, adapters 607, 606, and 612 may be connected to one or more I/O buses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 613 via user interface adapter 608 and display adapter 612. A keyboard 609, mouse 640, and speaker 611 can be interconnected to system bus 613 via user interface adapter 608, which may include, for example, a Super I/O chip integrating multiple device adapters into a single integrated circuit.

Thus, as configured in FIG. 6, processing system 600 includes processing capability in the form of processors 601, and, storage capability including system memory 614 and mass storage 604, input means such as keyboard 609 and mouse 640, and output capability including speaker 611 and display 615. In one embodiment, a portion of system memory 614 and mass storage 604 collectively store an operating system such as the AIX® operating system from IBM Corporation to coordinate the functions of the various components shown in FIG. 6.

Technical effects and benefits include the ability to construct evidence graphs where edges have features produced by a QA system that uses a corpus of expository text (e.g., textbooks and reference materials). This avoids the need to construct probabilistic knowledge bases or learn application-specific models.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
  creating an inference model via a computer processor, the creating comprising:
    receiving a training set that includes multiple scenarios, each scenario comprising one or more natural language statements, and each scenario corresponding to a plurality of candidate answers;
    constructing evidence graphs for each of the multiple scenarios based on the training set, wherein constructing the evidence graphs comprises for each scenario:
      extracting factors from the scenario; and
      generating intermediate nodes based on the extracted factors,
      wherein the factors are root nodes in the evidence graphs and the candidate answers are terminal nodes in the evidence graphs; and calculating weights for common features across the evidence graphs that will maximize a probability of the inference model locating correct answers from corresponding candidate answers across all of the multiple scenarios, wherein calculating the weights comprises assigning a highest weight to a factor having a largest number of unique terms relative to a selected domain; and in response to an inquiry from a user via the computer processor, the inquiry comprising a scenario, constructing, using the inference model, an evidence graph and recursively constructing formulas to express a confidence of each node in the evidence graph in terms of corresponding parents in the evidence graph.

2. The method of claim 1, wherein the constructing evidence graphs further includes generating questions for the factors and the intermediate nodes represent the generated questions.

3. The method of claim 1, wherein edges of the intermediate nodes are determined using a question answering (QA) system that assigns a confidence value and a feature vector to each edge.

4. The method of claim 1, wherein the candidate answers are expressed as a parameterized mathematical expression that matches semantics of the inference model.

5. The method of claim 1, wherein the inference model applies different weights to the factors.

6. The method of claim 1, wherein the scenario corresponds to a medical environment and the candidate answers indicate corresponding diagnoses.

* * * * *